(12) United States Patent
Fowler et al.

(10) Patent No.: US 7,953,493 B2
(45) Date of Patent: May 31, 2011

(54) OPTIMIZING SIZE OF IMPLANTABLE MEDICAL DEVICES BY ISOLATING THE POWER SOURCE

(75) Inventors: Robert Fowler, Danville, CA (US); Mark W. Cowan, Fremont, CA (US); N. Parker Willis, Atherton, CA (US); Axel F. Brisken, Fremont, CA (US); Debra S. Echt, Woodside, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 221 days.

(21) Appl. No.: 12/340,395

(22) Filed: Dec. 19, 2008

(65) Prior Publication Data

US 2009/0264965 A1    Oct. 22, 2009

Related U.S. Application Data

(60) Provisional application No. 61/016,869, filed on Dec. 27, 2007.

(51) Int. Cl.
*A61N 1/00* (2006.01)
(52) U.S. Cl. .......................................... 607/61
(58) Field of Classification Search ............... 607/5, 27, 607/32, 33, 61; 606/205; 600/459; 320/107, 320/108, 128, 130
See application file for complete search history.

(56) References Cited

U.S. PATENT DOCUMENTS

| | | |
|---|---|---|
| 3,659,615 A | 5/1972 | Enger |
| 3,693,627 A | 9/1972 | Berkovits |
| 3,698,398 A | 10/1972 | Berkovits |
| 3,735,756 A | 5/1973 | Richards et al. |
| 3,832,994 A | 9/1974 | Bicher et al. |
| 3,857,382 A | 12/1974 | Williams et al. |
| 3,939,844 A | 2/1976 | Peuignot |
| 3,942,534 A | 3/1976 | Allen et al. |
| 4,181,133 A | 1/1980 | Kolenik et al. |
| 4,256,115 A | 3/1981 | Bilitch |
| 4,265,228 A | 5/1981 | Zoll |
| 4,280,502 A | 7/1981 | Baker, Jr. et al. |
| 4,561,442 A | 12/1985 | Vollmann et al. |

(Continued)

FOREIGN PATENT DOCUMENTS

DE           4330680 A1      3/2005

(Continued)

OTHER PUBLICATIONS

Abraham et al., for the Miracle study group, "Cardiac Resynchronization in Chronic Heart Failure," N Engl J Med, 2002;346:1845-53.

(Continued)

*Primary Examiner* — George Manuel
*Assistant Examiner* — Robert N Wieland
(74) *Attorney, Agent, or Firm* — Kilpatrick Townsend & Stockton LLP (57) ABSTRACT

A wireless cardiac stimulation device comprising an implantable transmitter module housing a transmitter and a separately implantable battery module housing a battery for powering the transmitter and other device electronics via a subcutaneously routable electrical cable connecting the module is disclosed. The transmitter module contains a transmitter enclosure which comprises one or more ultrasound transducers. Having separate transmitter and battery modules allows implantation of the transmitter module closer to the target receiver implanted in tissue. A discrete battery module also enables easy replacement of the battery without disturbing the transmitter, which is highly desirable.

32 Claims, 5 Drawing Sheets

U.S. PATENT DOCUMENTS

| | | | |
|---|---|---|---|
| 4,577,633 A | 3/1986 | Berkovits et al. | |
| 4,651,716 A | 3/1987 | Forester et al. | |
| 4,690,144 A | 9/1987 | Rise et al. | |
| 4,830,006 A | 5/1989 | Haluska et al. | |
| 5,018,523 A | 5/1991 | Bach, Jr. et al. | |
| 5,063,928 A | 11/1991 | Grevis | |
| 5,103,129 A | 4/1992 | Slayton et al. | |
| 5,113,859 A | 5/1992 | Funke | |
| 5,165,403 A | 11/1992 | Mehra | |
| 5,170,784 A | 12/1992 | Ramon | |
| 5,174,289 A | 12/1992 | Cohen | |
| 5,193,539 A | 3/1993 | Schulman et al. | |
| 5,292,338 A | 3/1994 | Bardy | |
| 5,377,166 A | 12/1994 | Kuhn | |
| 5,405,367 A | 4/1995 | Schulman et al. | |
| 5,411,535 A | 5/1995 | Fujii et al. | |
| 5,433,731 A | 7/1995 | Hoegnelid et al. | |
| 5,674,251 A | 10/1997 | Combs et al. | |
| 5,749,909 A | 5/1998 | Schroeppel et al. | |
| 5,751,539 A | 5/1998 | Stevenson et al. | |
| 5,757,104 A | 5/1998 | Getman | |
| 5,766,227 A | 6/1998 | Nappholz et al. | |
| 5,800,464 A | 9/1998 | Kieval | |
| 5,814,089 A | 9/1998 | Stokes et al. | |
| 5,817,130 A | 10/1998 | Cox et al. | |
| 5,844,349 A | 12/1998 | Oakley et al. | |
| 5,871,506 A | 2/1999 | Mower | |
| 5,935,158 A | 8/1999 | Holmstrom et al. | |
| 5,978,204 A | 11/1999 | Stevenson | |
| 5,998,910 A | 12/1999 | Park et al. | |
| 6,037,704 A | 3/2000 | Welle | |
| 6,070,101 A | 5/2000 | Struble et al. | |
| 6,078,837 A | 6/2000 | Peterson et al. | |
| 6,110,098 A | 8/2000 | Renirie et al. | |
| 6,141,588 A | 10/2000 | Cox et al. | |
| 6,208,894 B1 | 3/2001 | Schulman et al. | |
| 6,223,079 B1 | 4/2001 | Bakels et al. | |
| 6,233,484 B1 | 5/2001 | Ben-Haim et al. | |
| 6,330,475 B1 | 12/2001 | Renirie et al. | |
| 6,366,816 B1 | 4/2002 | Marchesi | |
| 6,408,205 B1 | 6/2002 | Renirie et al. | |
| 6,424,234 B1 | 7/2002 | Stevenson | |
| 6,439,236 B1 | 8/2002 | Porter et al. | |
| 6,445,953 B1 | 9/2002 | Bulkes et al. | |
| 6,534,895 B2 | 3/2003 | Kadota et al. | |
| RE38,119 E | 5/2003 | Mower | |
| 6,628,989 B1 | 9/2003 | Penner et al. | |
| 6,645,145 B1 | 11/2003 | Dreschel et al. | |
| 6,647,292 B1 | 11/2003 | Bardy et al. | |
| 6,654,638 B1 | 11/2003 | Sweeny | |
| 6,671,547 B2 | 12/2003 | Lyster et al. | |
| 6,707,230 B2 | 3/2004 | Smith et al. | |
| 6,721,597 B1 | 4/2004 | Bardy et al. | |
| 6,754,528 B2 | 6/2004 | Bardy et al. | |
| 6,754,531 B1 | 6/2004 | Kroll et al. | |
| 6,764,446 B2 | 7/2004 | Wolinsky et al. | |
| 6,788,974 B2 | 9/2004 | Bardy et al. | |
| 6,798,716 B1 | 9/2004 | Charych | |
| 6,834,204 B2 | 12/2004 | Osteroff et al. | |
| 6,856,835 B2 | 2/2005 | Bardy et al. | |
| 6,983,185 B2 | 1/2006 | Ley et al. | |
| 7,010,350 B2 | 3/2006 | Kralik | |
| 7,024,248 B2 | 4/2006 | Penner et al. | |
| 7,198,603 B2 | 4/2007 | Penner et al. | |
| 7,200,437 B1 | 4/2007 | Nabutovsky et al. | |
| 7,283,874 B2 | 10/2007 | Penner | |
| 7,610,092 B2* | 10/2009 | Cowan et al. | 607/33 |
| 2003/0119153 A1 | 6/2003 | Moriya et al. | |
| 2004/0015104 A1 | 1/2004 | Goldberger | |
| 2004/0106963 A1* | 6/2004 | Tsukamoto et al. | 607/33 |
| 2004/0172083 A1 | 9/2004 | Penner | |
| 2004/0204744 A1 | 10/2004 | Penner et al. | |
| 2004/0243192 A1 | 12/2004 | Hepp et al. | |
| 2004/0260214 A1 | 12/2004 | Echt et al. | |
| 2005/0192639 A1* | 9/2005 | Bardy et al. | 607/5 |
| 2006/0052695 A1 | 3/2006 | Adam et al. | |
| 2006/0136005 A1 | 6/2006 | Brisken et al. | |
| 2006/0184204 A1 | 8/2006 | He | |
| 2007/0027508 A1 | 2/2007 | Cowan et al. | |
| 2007/0055184 A1 | 3/2007 | Echt et al. | |
| 2007/0060961 A1 | 3/2007 | Echt et al. | |
| 2007/0078490 A1 | 4/2007 | Cowan et al. | |
| 2007/0100384 A1 | 5/2007 | Fischell et al. | |
| 2007/0282374 A1 | 12/2007 | Sogard et al. | |
| 2008/0294208 A1 | 11/2008 | Willis et al. | |
| 2009/0018599 A1* | 1/2009 | Hastings et al. | 607/32 |
| 2009/0036777 A1* | 2/2009 | Zhang et al. | 600/459 |

FOREIGN PATENT DOCUMENTS

| | | |
|---|---|---|
| WO | WO 99/61058 A1 | 12/1999 |
| WO | WO 03/070323 A1 | 8/2003 |

OTHER PUBLICATIONS

ACC/AHA Task Force on Practice Guidelines, "Evaluation and Management of Chronic Heart Failure in the Adult," JACC 2002;38:2101-13.

Allessie et al., "Regional Control of Atrial Fibrillation by Rapid Pacing in Conscious Dogs," Circulation 1991;84:1689-97.

Ansalone et al., "Bi-ventricular Pacing I Heart Failure:Back to Basics in the Pathophysiology of Left Bundle Branch Block to Reduce the Number of Nonresponders," Am J Cardiol 2003;91:55F-61F.

Auricchio et al., "Cardiac Resynchronization Therapy: Current State of the Art," Circulation 2004;109:300-307.

Bardy et al., "The Totally Subcutaneous ICD System (The S-ICD)," PACE. 2002; 24,578.

Becker et al, "Suppression of Atrial Fibrillation by Multisite and Septal Pacing in a Novel Experimental Model", Cardiovascular Research 2001;54(2):476-481.

Bradley et al., "Cardiac Resynchronization and Death from Progressive Heart Failure: A Meta-Analysis of Randomized Controlled Trials," JAMA 2003;289:730-740.

Camm et al., Chapter 6: Nonpharmaceutical treatment of atrial fibrillation, In Atrial Fibrillation. Facts from Yesterday—Ideas for tomorrow. Futura Publishing Company, Inc., Armonk, NY, 1994, pp. 125-147.

Dalecki et al., "Effects of Pulsed Ultrasound on the Frog Heart: I. Thresholds for Changes in Cardiac Rhythm and Aortic Pressure," Ultrasound in Med. & Biol. 1993; 19:385-390.

Dalecki et al., "Effects of Pulsed Ultrasound on the Frog Heart: II. An Investigation of Heating as a Potential Mechanism," Ultrasound in Med. & Biol. 1993; 19:391-398.

Dalecki et al., "Thresholds for premature ventricular contractions in frog hearts exposed to lithotripter fields," Ultrasound in Med. & Biol. 1991; 17:341-346.

Daoud et al., "Implantation Techniques and Chronic Lead Parameters of Biventricular Pacing Dual-chamber Defibrillators," J Cardiovasc Electrophysiology 2002; 13:964-970.

Daubert et al., "Permanent Left Ventricular Pacing With Transvenous Leads Inserted Into The Coronary Veins," PACE 1998;21;239-245.

Daubert et al., "Use of Specifically Designed Coronary Sinus Leads for Permanent Left Ventricular Pacing: Preliminary Experience," PACE, 1997; 20: II-NASPE Abstract Apr. 17, 1997.

David Trial Investigators, "The Dual Chamber and VVI Implantable Defibrillator (David) Trial," JAMA 2002;288:3115-3123.

Deshmukh et al. "Direct His-bundle pacing: present and future," PACE 2004;27 [Pt.II]:862-70.

Ellenbogen et al., "Detection and Management of An Implantable Cardioverter Defibrillator Lead Failure," JACC. 2003;41:73-80.

Feldman et al, "Comparison of medical therapy, resynchronization and defibrillation therapies in heart failure trial (Companion)," Presented at ACC 2003 Late Breaking Clinical Trials, 1 page.

Franz, "Mechano-electrical feedback in ventricular myocardium," Cardiovascular Research. 1996; 32:15-24.

Gregoratos et al., ACC/AHA/NASPE 2002 guideline update for implantation of cardiac pacemakers and antiarrhythmia devices: a report of the American College of Cardiology/American Heart Association Task Force on Practice Guidelines (ACC/AHA/NASPE Committee to Update the 1998 Pacemaker Guidelines). Circulation. 2002; 106:2145-2161.

Hauser et al., "Feasibility and Initial Results of an Internet-Based Pacemaker and ICD Pulse Generator and Lead Registry," Pacing Clin Electrophysiol. Jan. 2001;24(1):82-87.

Hu et al., "Stretch-Activated Ion Channels in the Heart," J. Mol. Cell Cardiol. 1997; 29:1511-1523.

Johnson et al., "Adaptive Pacing During Ventricular Fibrillation," PACE 2003;26:1824-36.

Kalman J.M. et al, "Regional Entrainment of Atrial Fibrillation in Man", J Cardiovasc Electrophysiol 1991;7:867-76.

Kass et al., "Improved Left Ventricular Mechanics from Acute VDD Pacing in Patients with Dilated Cardiomyopathy and Ventricular Conduction Delay," Circulation 1999;99:1567-73.

Kenknight B.H. et al, "Regional Capture of Fibrillating Ventricular Myocardium" Circ Res 1999;77:849-55.retrieve from the Internet: <<http://circres.ahajournals.org/cgi/content/full/77/4/849>>.

Kohl et al., Stretch-Induced Changes in Heart Rate and Rhythm: Clinical Observations, Experiments and Mathematical Models. Progress in Biophysics & Molecular Biology, 1999; 71:91-138.

Kohl et al., "Sudden Cardiac Death by Commotio Cordis: Role of Mechano-Electrical Feedback," Cardiovascular Research, 2001; 50:280-289.

Leclercq et al, "Is Dual Site Better than Single Site Atrial Pacing in the Prevention of Atrial Fibrillation?" PACE 2000;23:2102-7.

Leclercq et al., "Systolic Improvement and Mechanical Resynchronization does not Require Electrical Synchrony in the Dilated Failing Heart with Left Bundle-Branch Block", Circulation 2002;106:1760-1763.

Leclerq et. al., "Acute Hemodynamic Effects of Biventricular DDD Pacing in Patients with End-Stage Heart Failure", JACC 1998;32:1825-1831.

Lee et al., "Effect of implantable Defibrillators of Arrhythmic Events and Mortality in the Multicenter Unsustained Tachycardia Trial," Circulation. 2002; 106:233-238.

Linde et al., "Long-Term Benefits of Biventricular Pacing in Congestive Heart Failure: From the Multisite Stimulation in Cardiomyopathy (MUSTIC) Study", J Am Coll Cardiol 2002;40:111-118.

Miracle Trial Investigators, "Combined Cardiac Resynchronization and Implantable Cardioversion Defibrillation in Advanced Heart Failure: the Miracle ICD Trial," JAMA 2003;289:2685-2694.

Mirza et al, "Biatrial Pacing for Paroxysmal Atrial Fibrillation", J Am Coll Cardiol 2002;40:457-463.

Moss et al., "Prophylactic Implantation of a Defibrillator in Patients with Myocardial Infarction and Reduced Ejection Fraction," N Engl J Med. 2002; 346:877-933.

Niehaus et al., "Non-Contact Cardiac Stimulation with locused Ultrasound Pulses," PACE 2003: 26:1023.

Nielsen et al., "A Randomized Comparison of Atrial and Dual-Chambered Pacing in 177 Consecutive Patients With Sick Sinus Syndrome," J Am Coll Cardiol 2003;42:614-623.

Nolte et al., "Mechanically Induced Ventricular Extrasystoles in the Isolated Perfused Guinea-Pig Heart," Arzneim.-Forsch/Drug Research. 1987; 37(11): 1025-1029.

Peschar et al., "Left Ventricular Septal and Apex Pacing for Optimal Pump Function in Canine Hearts," J Am Coll Cardiol, 2003;41:1218-26.

Reiter et al.., "Effects of Mechano-Electrical Feedback: Potential Arrhythmogenic Influence in Patients With Congestive Heart Failure," Cardiovascular Research, 1996; 32:44-51.

Smailys et al., "Investigation of the Possibilities of cardiac Defibrillation by Ultrasound," Resuscitation, 1981; 9:233-242.

Sowton, "Clinical Results with the Tachylog Antitachycardia Pacemaker", PACE 1984; 7(Part II):1313-1317.

Tacker, Chapter 1: Fibrillation causes and criteria for defibrillation. In Defibrillation of the Heart. Tacker, WA, ed. Mosby-Year Book, Inc., St. Louis, Missouri, 1994, pp. 1-14.

The Antiarrhythmics Versus Implantable Defibrillators (AVID) Investigators, "A Comparison of Antiarrhythmic Drug Therapy with Implantable Defibrillators in Patients Resuscitated from Near Fatal Ventricular Arrhythmias," N Engl J Med.,1997;337: 1576-1583.

Valls-Bertault et al., "Adverse Events with Transvenous Left Ventricular Pacing in Patients with Severe Heart Failure: Early Experience from a Single Centre," Europace, 2001;3:60-63.

Warren et al., "Clinical Evaluation of Automatic Tachycardia Diagnosis by an Implanted Device", PACE 1986;9 (Part II):1079-1083.

International Search Report and Written Opinion of PCT Application No. PCT/US2008/088207, mailed Apr. 16, 2009, 11 pages total.

\* cited by examiner

OPTIMIZING SIZE OF IMPLANTABLE MEDICAL DEVICES BY ISOLATING THE POWER SOURCE

CROSS-REFERENCES TO RELATED APPLICATIONS

This application claims the benefit of the following provisional application: 61/016,869, filed on Dec. 27, 2007. The full disclosure of this prior filing is incorporated herein by reference.

The subject matter of this application is related to that of the following commonly owned patent application Ser. No. 10/315,023. The full disclosure of this prior filing is incorporated herein by reference but the benefit of the filing dates is not being claimed.

BACKGROUND OF THE INVENTION

1. Field of the Invention

The field of the present invention relates generally to implanted devices for tissue stimulation, monitoring, and other therapeutic or diagnostic functions, and specifically to implantable devices for the stimulation of cardiac tissue, for example pacemakers or implantable cardioverter-defibrillators (ICDs). More specifically, it pertains to such devices utilizing wireless energy transfer, for example through ultrasonic means.

2. Description of the Background Art

Conventional cardiac pacemaker and defibrillator systems comprise Implantable Pulse Generators (IPGs) constructed with a single hermetically-sealed enclosure that contains the electronic control circuitry and battery components. The mass of an IPG for a conventional cardiac pacemaker is primarily dependent upon the volume and weight of the enclosed battery that powers the electronic control elements and stimulation energy of the IPG.

In order to have an IPG of acceptable size and weight for implantation in patients, the batteries on average do not last as long as the patients' lifetime. Cardiac pacemaker and defibrillator battery longevity ranges from about 3-9 years (Hauser et al., "Feasibility and Initial Results of an Internet-Based Pacemaker and ICD Pulse Generator and Lead Registry," Pacing and Clinical Electrophysiology (PACE) 2001; 24:82-87). Therefore, many patients undergo multiple surgical procedures to replace the IPG.

For ease of insertion of pacing leads into the vasculature, the IPG is normally located subcutaneously in the pectoral region of the chest. This location is surgically accessible and near the typically used entry sites for the vascular leads. There is latitude with regards to the placement of the IPG enclosure. However, because it is connected to leads, the location and surgical process must consider lead insertion into a vascular access. Most often, the IPG is placed in a shallow subcutaneous pocket located in the upper left aspect of the chest, several centimeters below the clavicle. Venous access is then accomplished via the subclavian, cephalic, or axillary veins. This location generally allows the patient full range of movement with minimal discomfort. For example, see Hauser et al., 2001.

An ultrasound based Wireless Cardiac Stimulation (WiCS™) system has been disclosed in currently pending applications by the applicant (e.g., U.S. patent application Ser. No. 11/315,023). This system employs ultrasonic energy transfer from a subcutaneously implantable controller-transmitter device (C-T), which is directed towards one or more receiver-stimulator (R-S) devices implanted at desired sites in the heart, for example in the left ventricle. Ultrasonic transducers and circuitry in the R-S convert the transmitted ultrasonic energy into an electrical signal capable of stimulating the cardiac tissue. The WiCS™ system, C-T, and R-S are described in co-pending U.S. patent applications Nos. (Publication Number) 20060136004, 20060136005, 20070027508, 20070055184, 20070078490 and 20070060961 and Ser. No. 11/752,775, which are herein incorporated by reference in their entirety.

In the disclosed WiCS™ system, the C-T contains ultrasound elements as well as housing for the electronic control circuitry and battery. The C-T transmits ultrasound through the chest wall to the location of the R-S which may be placed in the left ventricle of the heart or any other heart location. In one preferred embodiment of the system, the transmitting aperture is located with a direct line of transmission between the C-T and the R-S—the direct line avoiding both bone and lung tissue to minimize transmission losses. Thus, it is desirable to place the transmitting aperture anteriorly over the rib cage of the left chest, and further desirable to align as much of the aperture of the transmitter as possible with the intercostal space between two ribs. It is still further desirable to tightly affix the transmitting aperture in the preferred location so that other factors, such as patient movement, do not disturb its position.

However, it can be observed that a significant portion of the general population, including potential recipients of the WiCS™ system, do not have significant thickness of muscle or fat tissue in the left anterior chest in the area of the 4th, 5th, and 6th ribs, which are preferred locations for such a device. Therefore, to improve patient comfort and to provide the largest usable aperture, it would be desirable to optimize the volume of devices implanted in this area, particularly by reducing the thickness of the device. To reduce the possible movement or dislodgement of the device, it would also be desirable to optimize its weight, particularly by reducing the mass of the device. The present embodiments address these challenges, as well as providing further advantages, as disclosed herein. Alternatively, other implant sites that have an unobstructed acoustic path between the C-T and R-S, for example, pericardial placement or subcostal placement, would be more practical if the C-T could remain undisturbed when replacing the battery.

BRIEF SUMMARY OF THE INVENTION

Embodiments of the present invention are directed to wireless cardiac stimulation C-T devices comprising two separately implantable modules. The first module (transmitter module) houses a transmitter while the second houses a battery (battery module) for powering the system. The battery powers the transmitter via an implantable cable connecting the two modules. The control electronics could be housed in either module. The control electronics could include means for receiving instructions or programming from an external communications device and circuits for operating the transmitter and could be preferably located in the transmitter module.

The cable supplies power from the battery to the transmitter module. The cable can further comprise an antenna to facilitate communication between the implantable modules and an external programming module for initial setup or clinical monitoring of the system performance. In one embodiment, the antenna is incorporated into an outer-facing surface of the battery enclosure or in an alternative embodiment the antenna is incorporated into the cable, and the system comprises radio circuitry within the battery enclosure or the transmitter enclosure.

The system further comprises one or more sensing electrodes incorporated onto the surface of one or both the implanted modules or the cable. These electrodes could sense electrograms and the sensed information could be advantageously used for controlling the generation and transmission of acoustic energy from the transmitter module. The cable could further have connectors at both ends. In one embodiment, the cable is permanently attached to the transmitter module and the other end of the cable terminates in connectors that can be detachably attached to connectors on the battery module. This facilitates replacement of the battery module without having to disturb the implanted transmitter module.

In one embodiment, the enclosures comprise one or more features, such as localization or immobilization devices, e.g., suture points, incorporated onto their exteriors to facilitate their alignment. For example, the transmitter module may be localized over an intercostal space to align the transmitter with a receiver-stimulator in the heart and the battery module may be localized to the abdominal area to align its placement relative to the transmitter and connecting cable. The enclosures may be secured to underlying fascia, thereby stabilizing the modules relative to their respective chosen locations and preventing their dislodgement or movement due to patient movement.

Another aspect of the invention relates to a tissue stimulation system comprising an implantable transmitter module, a battery module and one or more receiver-stimulators wherein the transmitter and battery modules are connected by a cable, and the transmitter module comprises a transducer array. The transmitter module can additionally comprise various ASICs for generating, controlling and transmitting acoustic energy from the transmitter module. The circuits could be configured to be optimally distributed inside the transmitter module and one such configuration being where the ASICs are stacked on top of the transducer array, with the transducer array closest to the heart.

In yet another aspect of this invention, the tissue pocket that is created to house the transmitter module is slightly smaller than the transmitter module so that the transmitter module fits snugly in the space. Additionally, the transducer array is sized to be wider than the intercostal space such that at least a portion of the transducer array, the target tissue and the receiver stimulators implanted in the target tissue are always within the acoustic transmission path without being obscured by intervening tissues such as rib and lung.

Another aspect of this invention is methods and systems for optimizing energy transmission in implantable ultrasound transducer arrays comprising activating one or more ultrasound transducers to transmit acoustic energy towards an implanted receiver-stimulator, where the receiver-stimulator is configured to receive the acoustic energy and convert the received acoustic energy into electrical energy output. By monitoring the electrical energy output of the receiver-stimulator, it can be determined whether the ultrasound transducers of the controller-transmitter are obscured by intervening tissue. Additionally, this information about the unobscured transducers can be advantageously used for transmitting acoustic energy towards an implanted receiver-stimulator using the unobscured transducers, where the receiver-stimulator converts the received acoustic energy into electrical energy output to stimulate tissue at the location of the receiver-stimulator.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION OF THE INVENTION

In the following description, for purposes of explanation, numerous specific details are set forth in order to provide a thorough understanding of the invention. It will be apparent, however, to one skilled in the art that the invention can be practiced without these specific details.

An ultrasound based Wireless Cardiac Stimulation (WiCS™) system comprising two separate C-T enclosures is disclosed. The first enclosure houses one or more transducers and electronics to control the operation of the transducer(s). The second enclosure houses a battery. The battery powers the transducer(s) and electronics via an electrical cable connecting the enclosures.

Figure 1A:
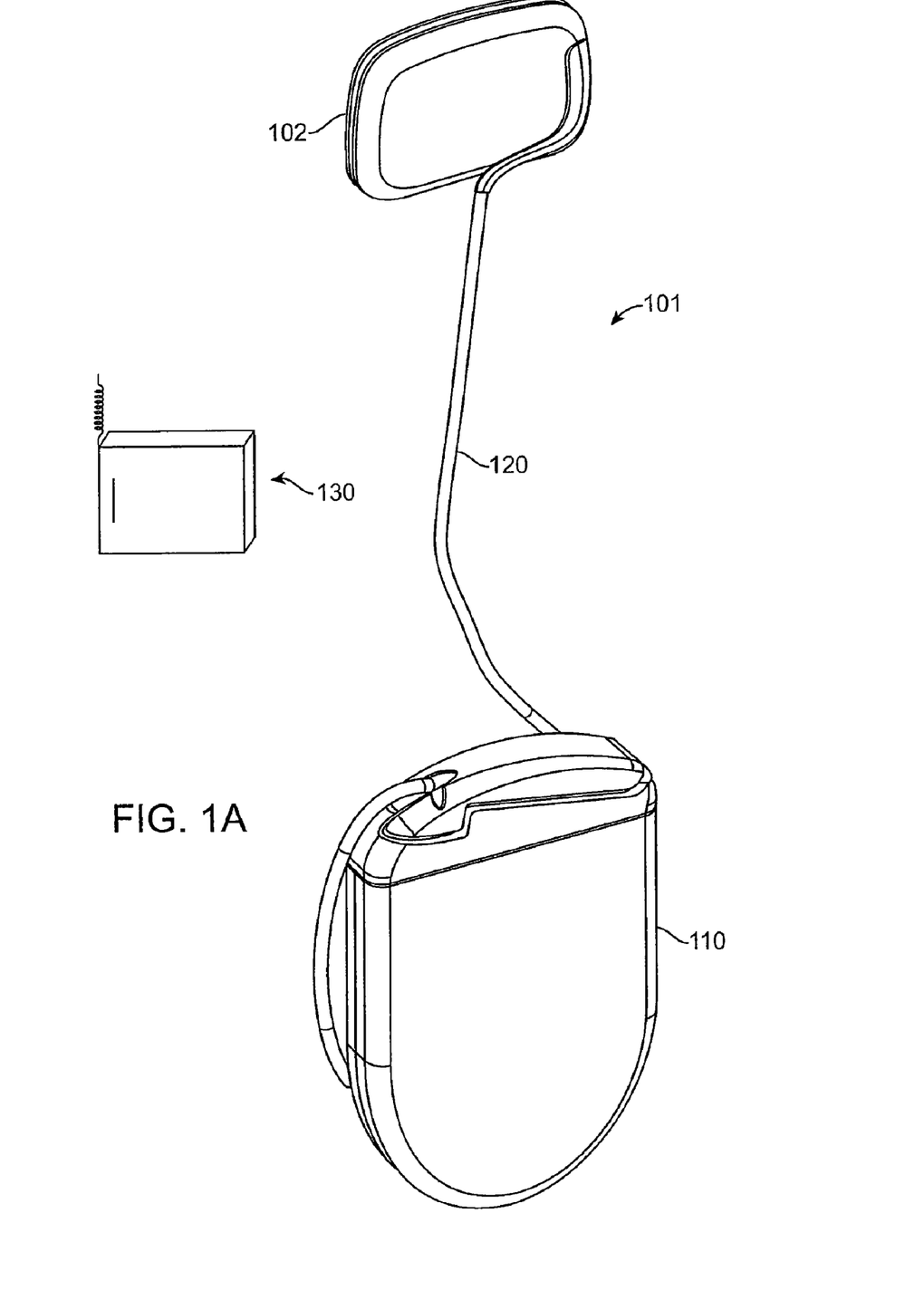
FIGS. 1A, 1B and 1C are diagrammatic views of a wireless cardiac stimulation system having separately implantable transmitter and battery modules, in accordance with an embodiment of the present invention.
Figure 1B:
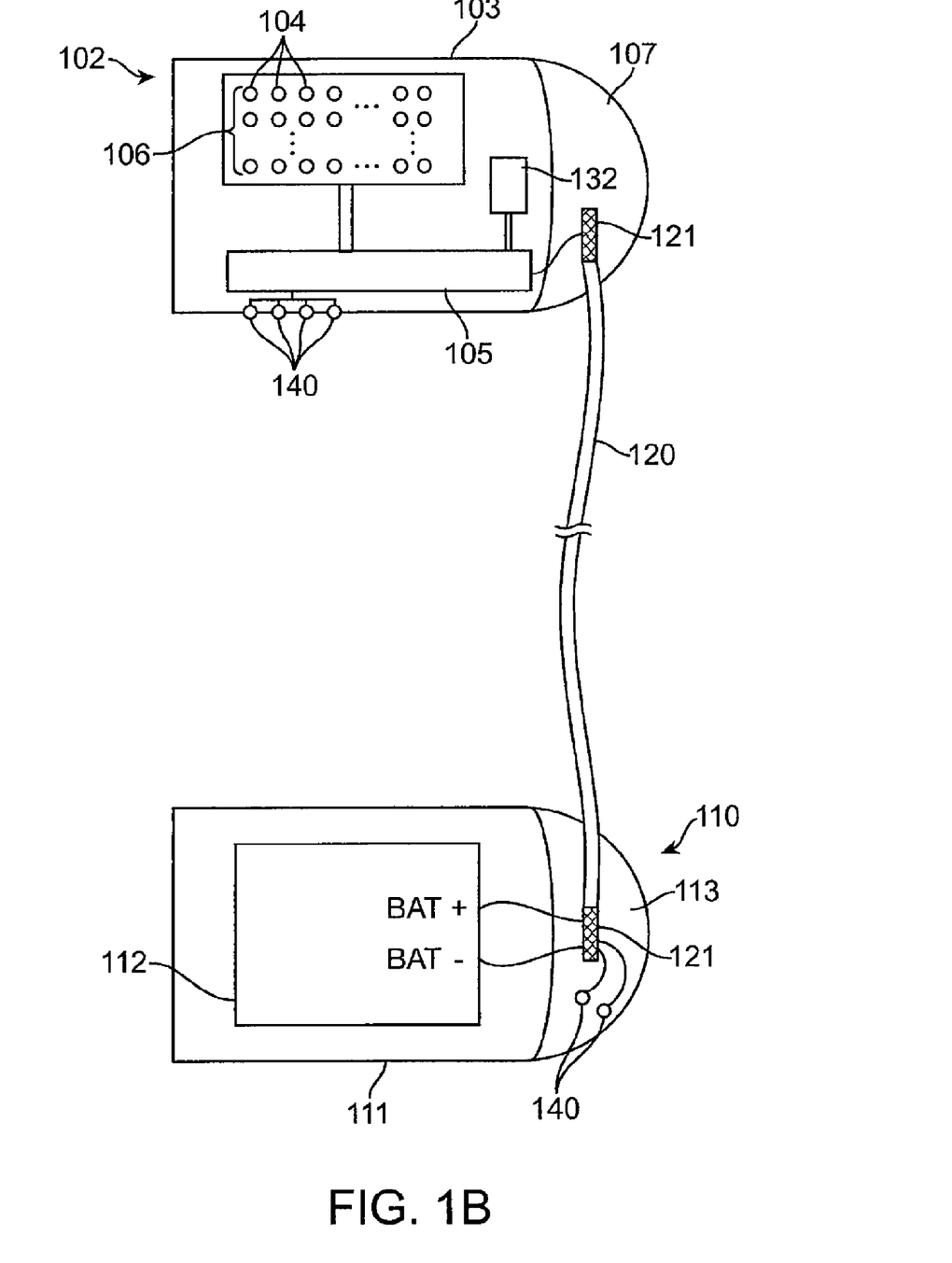

FIGS. 1A and 1B illustrate components of a wireless cardiac stimulation system 101, in accordance with an embodiment of the present invention. The WiCS™ system comprises a transmitter module 102, a battery module 110, a header or connector block 107, a cable 120, an external programmer 130 and one or more implantable receiver-stimulator units (not shown). Transmitter module 102 comprises a transmitter enclosure 103 which houses one or more ultrasonic transducers 104 and electronics 105 for the generation and control of the ultrasound transmission. As will be known to one of ordinary skill in the art, using modem microelectronics methods such components may be made very small, thus causing a reduction in the overall size, thickness, and weight of the transmitter module 102. In one embodiment, and as shown in FIG. 1B multiple ultrasonic transducers (104) are arranged as a transducer array 106. Internal connections between the electronics 105 and the transducers 104 in the transducer array 106 are not shown in detail in FIG. 1B. Hundreds of such transducers 104 may be arranged in the array 106. This poses special demands on establishing the electrical connections between the transducers and the electronics 105 that control the desired functioning of these transducers. Hence, it is desirable to locate the control electronics 105 proximate to the transducer array 106 inside the enclosure 103. In one embodiment, different components of the transmitter module can be stacked on top of each other. For example, the transducer array 106 could be the bottom most layer (facing the heart), with the transmit electronics (transmit ASIC) organized on top of the transducer array, and the control electronics 105 (control ASIC) layered over the transmit ASIC. The sensing electrodes 140 could be optimally distributed about the periphery of the outermost surface of the transmitter module.

In one embodiment, the transmitter module 102 may be approximately 2.5 cm×3.5 cm with a thickness of about 8 mm, allowing it to house a transducer array of approximately 2 cm×3 cm. Other dimensions are possible, as will be known to those of skill in the art.

Battery module 110 comprises a battery enclosure 111 which houses a battery cell 112 used to power the transmitter module 102. A header or connector block 113 is incorporated onto the battery enclosure 111. The battery module 110 may likely be larger, thicker, and/or heavier than the transmitter module 102, but such increased dimensions and weight are not an issue since slight movement or migration of the battery module 110 will not affect transmitter performance. One skilled in the art would recognize that in an alternative embodiment (not shown), some or all of the electronics circuitry 105 could be located in battery module 110. In such an embodiment, the transmitter module 102 could be even smaller than the embodiment where the electronics are present in the transmitter module 102. The electrical connections between the modules 102 and 110 could be established using appropriate connector and wiring that runs as part of the cable 120.

In one embodiment, the battery module 110 occupies a volume of about 35 cc. Using current battery technology, a battery module of such size would provide for approximately a 10 Amp-hour battery capacity. Using nominal transmission conditions to an R-S, this may provide approximately 3 years of service life for the device. It is contemplated that with advances in battery technology, the dimensions of the battery module 110 may be reduced without loss of battery capacity, or alternatively the battery module 110 may provide longer battery service life at approximately the same dimensions.

A cable 120 connects the two modules 102 and 110 and is preferably routed subcutaneously. In one embodiment, cable 120 comprises an electrical cable and allows battery cell 112 to power the transmitter module 102. The cable 120 could be thin, for increased patient comfort and ease of subcutaneous routing.

In one embodiment, one or both ends of the cable 120 are terminated in connectors 121 to facilitate implantation of the enclosures. While the connectors 121 may be of similar design and construction to current implantable connector systems (such as IS-1, DS-1, LV-1) used in pacemakers and ICDs, it is important for safety reasons that connectors 121 used on the present wireless cardiac stimulation device 101 not be able to accept or connect to conventional pacemakers, ICDs, pacing lead wires, or defibrillator lead wires. In one embodiment, the cable 120 is permanently attached to the transmitter module 102 or alternatively permanently attached to battery module 110, in which case only one end of the cable is terminated with connectors 121.

Figure 1C:
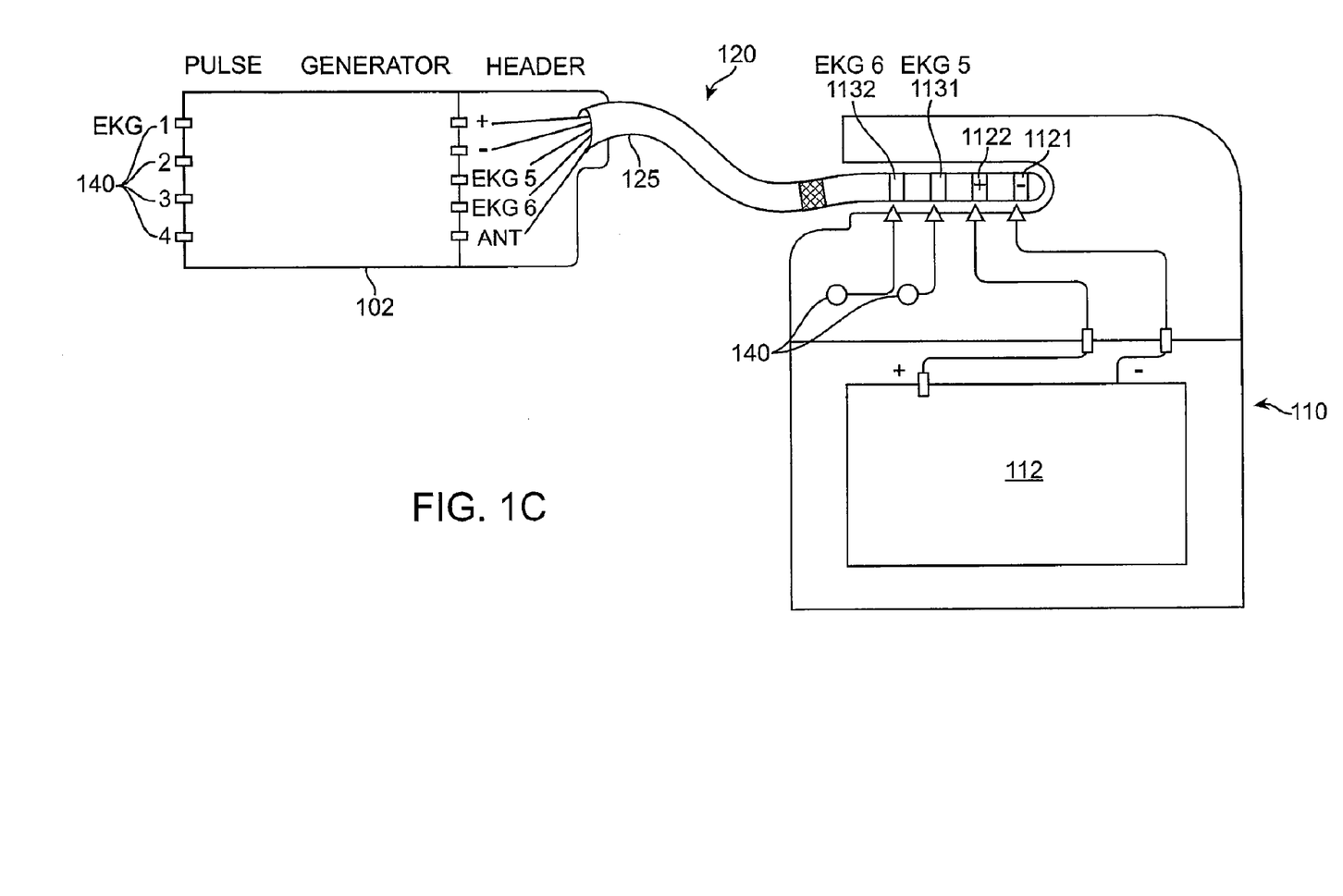

FIG. 1C shows various components of the cable 120. Cable 120 contains wires to connect the terminals 1121 and 1122 of the battery cell 112. Additionally it has wires connecting sensing electrodes 1131 and 1132 from the battery enclosure 110 to the transmitter assembly 102. Finally, the cable also has a shield 125 which may be braided, served or of similar construction that acts as the antenna and facilitates efficient communication between the devices and the external programmer 130 (shown in FIG. 1A).

The transmitter module 102 and the battery module 110 are configured to be separately implantable. In one embodiment, the transmitter module 102 is implanted subcutaneously to be centered above an intercostal space, typically between the fourth and fifth ribs. The battery module 110 is typically implanted below the transmitter module 102 at about 8 to 15 cm away from the transmitter module 102, as illustrated in FIG. 2B. Procedural steps for implanting the transmitter module 102 and the battery module 110 are illustrated in FIG. 2A.

Figure 2A:
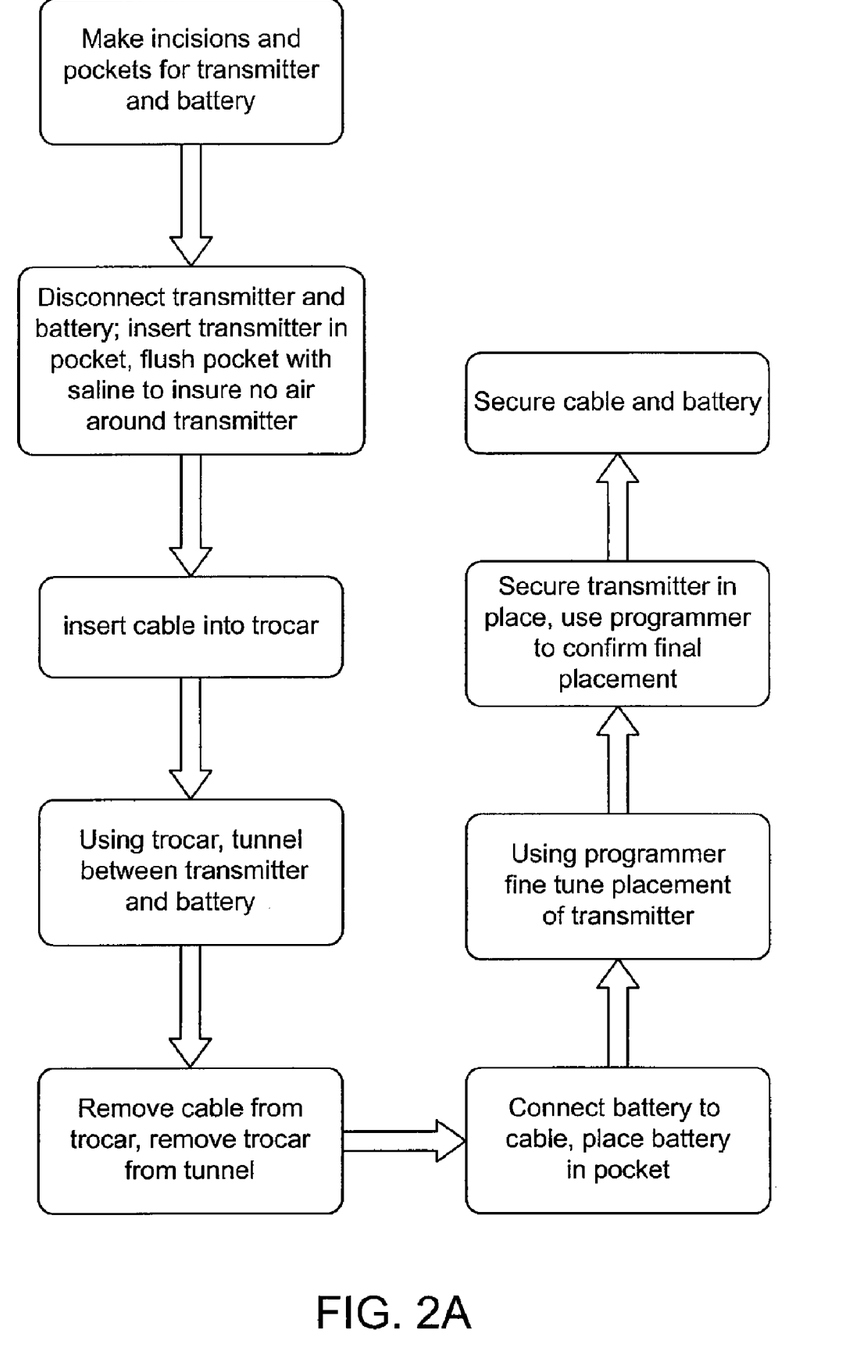
FIGS. 2A and 2B are diagrammatic views of a wireless cardiac stimulation system implant process steps and as it is implanted in a patient, in accordance with an embodiment of the present invention.
Figure 2B:
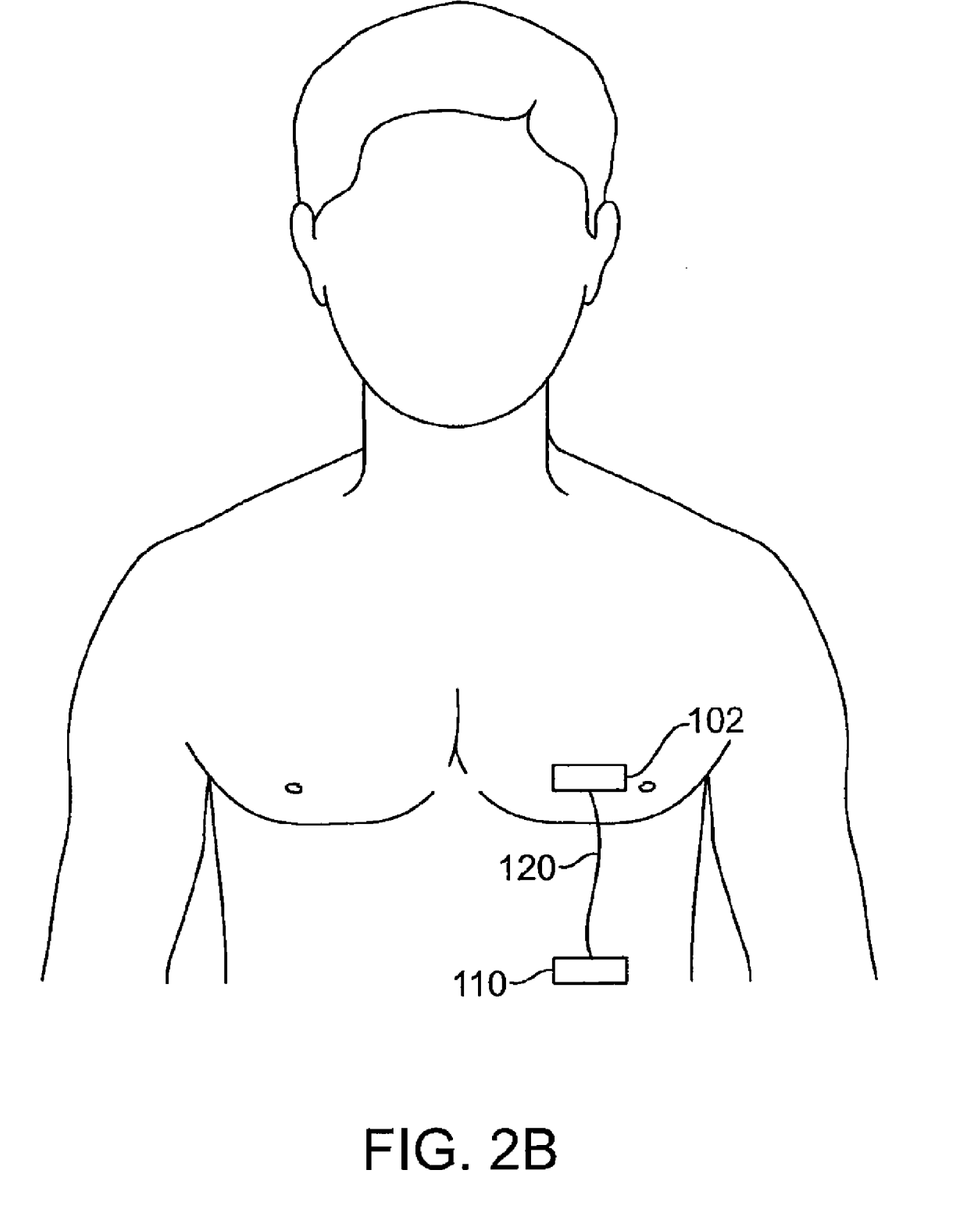

As shown in FIG. 2A, the transmitter and battery modules are implanted by first making a skin incision and then creating a subcutaneous tissue pocket in the region of an intercostal space overlying an acoustic window. The pocket is made to be slightly smaller than the transmitter module so that the transmitter module fits snugly in the space. This tissue pocket should be centered between two ribs, such that when secured, the transmitter module is centered in the pocket in order to optimize the position of the transmitter module between two ribs such that the aperture of the transducer array would be centered above the intercostal space. The transmitter module and the aperture of the transducer array may be oversized for the space and extend slightly over the ribs. The transmitter is now placed in the pocket. The second incision is made about 10 cm directly below the first incision and a second subcutaneous pocket is made to fit the battery module 110. Then, using a tunneling instrument, such as a trocar, a channel is created between the two incisions and the cable is inserted into one of the incisions and exits through the second incision, leaving the cable routed between the two incisions. In the case where the cable is permanently attached to the transmitter module then the cable would be routed starting with the transmitter module pocket. The battery module 110 is placed in the pocket created around the second incision. The cable 120 is then connected to the battery module 110. The transmitter module 102 and battery module 110 are sutured to the fascia. The skin incisions are closed using standard techniques. This leaves both modules fastened in place and connected subcutaneously via the cable 120. While the present embodiments describe the battery module 110 placed at a distance below the transmitter module 102, it is possible to implant the battery module 110 in other locations, with the cable 120 routed between the two modules. For example, the transmitter module could be located under the left breast and the battery module on the right side of the chest under the right breast with the cable 120 routed across and over the sternum.

Unlike conventional cardiac pacemakers, it is an object of the present embodiments to achieve and maintain an efficient acoustic transmission path from the transmitter module 102 to one or more receiver-stimulator devices (R-S) implanted inside the heart. In order to achieve such an acoustic path, the transmitter module 102 is subcutaneously implanted on the left chest wall overlying the heart. In one embodiment, the transmitter module 102 is sutured on the fascia over the intercostal muscle so that the transducer array is aligned between the 4th and 5th, or between the 5th and 6th ribs. Patients will undergo specific testing, such as acoustic window assessment testing, to determine an optimal location for transmitter module 102.

In one embodiment comprising a transducer array 106, the transmitter module 102 is sized wider than the intercostal space over which it is sutured. Optionally, since some of the transducers 104 may be obscured by ribs, or the transmitter may move with breathing, only an unobscured group of the transducers of the array 104 need be used to transmit acoustic energy. One technique is to determine such a group at the time of implantation or during clinical monitoring, with the help of an external programming module described below. Transducers 104 in the transducer array 106 may be activated in a pre-determined pattern sequentially or in groups, for example in a raster scan pattern, and reception by one or more receiver-stimulators monitored to determine whether the activated transducers are obscured or not, such that unobscured transducers 104 may be chosen for transmission. Optionally, such a raster pattern may be employed during the operation of the transmitter module 102 to compensate for newly obscured transducers 104 as a result of a change in the spatial relationship of transmitter module 102 and the R-S. Details for optimizing energy transmission from the transmitter, and one such optimization method is to use only unobscured transducers of the array, can be found in co-pending U.S. patent application Ser. No. 11/752,775 by applicant.

To optimize performance of the system, it is desirable to prevent or minimize movement of the transmitter module 102. One way to achieve this is by suturing the enclosure 103 to the fascia covering the ribs and intercostal muscles, or to the fascia of the pectoralis muscle if it is present. In one embodiment, the transmitter enclosure 103 incorporates onto its exterior one or more features, such as suture points, to facilitate its alignment between two ribs, and by which it may be secured to the underlying fascia. Alternatively, or additionally, the suture points may be incorporated in the cable 120 or the connector 121 of the device.

Separation of the battery cell 112 to a separate module rather than incorporating it into the transmitter module 102 has numerous advantages. For example, one advantageous aspect of the present embodiments is that battery depletion does not necessitate surgical access to the transmitter module 102 for battery replacement followed by a repeat of the acoustic transmission testing, alignment, and fixation of the transmitter module 102 to the body. Instead, the separately implanted battery module 110 is accessed and the battery module 110 is replaced or explanted without disturbing or explanting the transmitter module 102.

It is another advantageous aspect that the transmitter module 102 of the present embodiments has a reduced mass and size which minimizes temporary or permanent migration of the transmitter module 102 due to patient movement or gravity.

Furthermore, many patients tend to have little subcutaneous tissue, either muscular or adipose, in this region of the chest wall. Segregation of the battery cell 112 from the transmitter module 102, and the resulting reduction in the size and thickness of the transmitter implant, contributes to patient comfort and tolerance of the implanted transmitter module 102 without sacrificing battery life.

Another important advantage gained from separately implanting the battery module 110 and the transmitter module 102 relates to communication between the devices or components of the WICS™ system 101; particularly between the implanted devices and an external programming module. In one embodiment, the wireless cardiac stimulation system 101 utilizes radiofrequency communications to communicate with an external programmer unit 130 for initial setup and clinical monitoring. In one embodiment, the radiofrequency is in the Medical Implant Communications Service (MICS) band of approximately 402-405 MHz.

To facilitate low power transmission from the wireless cardiac stimulation system 101 through the skin to the external programming module 130, a communication antenna is used in conjunction with radio circuitry 132 (shown in FIG. 1B). In one embodiment, cable 120 encases an antenna for the wireless cardiac stimulation system 101, obviating the need for incorporating the antenna into the packaging of the transmitter module 102 or the battery module 110. Incorporating the antenna in the cable 120 has the advantage of compensating for some of the losses that occur when transmitting and receiving RF energy through body tissue. In another embodiment, a separate communication antenna is used comprising a loop design, wherein the loop is designed to be as large as possible, located external to any metal housing, and located as shallow in the patient's body as possible. Though the actual radio circuitry 132 may be located in either module 102 or 110, the antenna loop itself can be incorporated onto the outer-facing surface of the battery module 110, which will likely be the larger of the two modules 102 and 110 (due to the generally larger size of the battery cell 112). In an embodiment wherein the radio circuitry 132 is located within the transmitter module 102, the connections to the antenna are carried through the cable 120 routed between the two modules.

Optionally, the battery enclosure 111 and/or the transmitter enclosure 103 comprise one or more electrodes 140 (shown in FIG. 1C) for sensing electrogram signals. Electrodes 140 are incorporated onto the exterior surfaces of the enclosures. These electrodes are connected to amplifiers to process electrogram signals that can be used to provide the requisite sensing of electrical outputs from the receiver-stimulator in order to determine unobstructed transducers in the transducer array 106, or in order to evaluate effectiveness of stimulation by sensing physiologic events. Signals registered by the sensing electrodes could also be advantageously used for monitoring the performance of the transmitter by observing whether the desired electrical output of the R-S is achieved.

Although the detailed description contains many specifics, these should not be construed as limiting the scope of the invention but merely as illustrating different examples and aspects of the invention. Particularly, while heart tissue is used as the target tissue to illustrate the invention, it should be noted that the target tissue could be other tissues which could benefit from the separation of the transmitter and battery modules. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as described here.

What is claimed is:

1. A tissue stimulation system comprising:
an implantable battery module configured to house a battery to power a transmitter module;
wherein the transmitter module is separately implantable and comprises a transmitter enclosure and is configured for transmitting acoustic energy to one or more receiver-stimulator devices implantable in the tissue;
wherein the battery module and the transmitter module are connectable by an implantable cable wherein the cable conducts power from the battery to the transmitter module;
wherein the cable comprises an antenna, and the antenna is configured to facilitate a low power radiofrequency communication link between at least one of the implantable modules and an external programming module.

2. The system of claim 1 further comprising electronic circuitry for communication between an external device and the at least one implantable module.

3. The system of claim 2, wherein the antenna is further configured to facilitate initial setup or clinical monitoring of the system performance.

4. The system of claim 2, further comprising radio circuitry which is connected to the antenna to process a signal over the radiofrequency communication link.

5. The system of claim 1, further comprising one or more sensing electrodes incorporated onto the surface of one or both of the implantable modules or the cable.

6. The system of claim 5, wherein the cable further comprises one or more electrode connections.

7. The system of claim 1, wherein the battery module can be explanted without explanting the transmitter module.

8. A tissue stimulation system comprising:
an implantable transmitter module, the transmitter module configured to transmit acoustic energy to one or more receiver-stimulators implantable in the tissue;
wherein the transmitter module is adapted to draw power from a battery housed in a separately implantable-battery module, the battery module and the transmitter module connectable by an implantable cable, wherein the cable conducts power from the battery to the transmitter module;
wherein the cable comprises an antenna, and the antenna is configured to facilitate a low power radiofrequency communication link between at least one of the implantable modules and an external programming module.

9. The system of claim 8, further comprising electronic circuitry for communication between an external device and the at least one of the implantable module.

10. The system of claim 9, wherein the antenna is further configured to facilitate initial setup or clinical monitoring of the system performance.

11. The system of claim 9, further comprising a radio circuitry which is connected to the antenna to process a signal over the radiofrequency communication link.

12. The system of claim 8, further comprising one or more sensing electrodes incorporated onto the surface of one or both of the implantable modules.

13. The system of claim 8, wherein the cable comprises one or more electrode connections.

14. The system of claim 8, wherein the transmitter module comprises one or more features incorporated onto its exterior to facilitate its alignment overlying an intercostal space and by which it may be secured to underlying fascia, thereby stabilizing the transmitter module relative to the intercostal space and preventing its dislodgement or movement due to patient movement.

15. The system of claim 14, wherein the transmitter module is wider than the intercostal space, thereby allowing the transmitter module to be stably positioned relative to the intercostal space to optimize the use of an acoustic window.

16. The system of claim 8, wherein one end of the cable is permanently attached to the transmitter module, and the other end is attached to the battery module using releasable connectors.

17. The system of claim 8, wherein the transmitter module comprises a transducer array, wherein the transducer array is wider than an intercostal space in which the transmitter module is localized.

18. The system of claim 17, wherein the transducer array targets the receiver-stimulator is through an acoustic window.

19. A method of optimizing energy utilization in ultrasound transducer arrays comprising:
activating one or more ultrasound transducers to transmit acoustic energy towards an implanted receiver-stimulator, wherein the receiver-stimulator is configured to receive the acoustic energy and convert the received acoustic energy into electrical energy output;
monitoring the electrical energy output; and
determining whether the ultrasound transducers are obscured by intervening tissue, based on the monitored output.

20. The method of claim 19, further comprising activating those transducers that have been determined to be unobscured by intervening tissue and transmitting acoustic energy towards an implanted receiver-stimulator, wherein the receiver-stimulator converts the received acoustic energy into electrical energy output to stimulate tissue at the location of the receiver-stimulator.

21. The method of claim 19, wherein the ultrasound transducer array is implantable and is located in a subcutaneous pocket above an intercostal space.

22. The method of claim 21, wherein the transducer array is wider than the intercostal space.

23. A system for optimizing energy utilization in ultrasound transducer arrays comprising:
a controller-transmitter configured to activate one or more ultrasound transducers of a transducer array that transmit acoustic energy towards an implanted receiver-stimulator, wherein the receiver-stimulator is configured to receive the acoustic energy and convert the received acoustic energy into electrical energy output delivered to pacing electrodes at the location of the receiver-stimulator;
one or more sensing electrodes that are connected to the controller-transmitter and are configured to monitor the electrical energy output; and circuitry configured to identify the ultrasound transducers of the transducer array that are obscured by intervening tissue based on the monitored electrical energy output.

24. The system of claim 23, further comprising activating the transducers in a pre-determined pattern.

25. The system of claim 23, further comprising activating those transducers that have been identified to be unobscured by intervening tissue to target the receiver-stimulator with sufficient acoustic energy that the electrical energy output stimulates the tissue at the location of the receiver-stimulator.

26. The system of claim 23, wherein the ultrasound transducer array is implantable in a subcutaneous pocket above an intercostal space.

27. The system of claim 26, wherein the transducer array is wider than the intercostal space.

28. A tissue stimulation system comprising:
an implantable transmitter module;
a discrete, implantable battery module;
one or more implantable receiver-stimulators;
wherein the transmitter module comprises a transducer array comprising one or more ultrasound transducers and configured to transmit acoustic energy towards one or more of the receiver-stimulators;
the transmitter module is adapted to draw power from a battery housed in the implantable battery module; and the battery module and the transmitter module are connectable by an implantable cable;
wherein the cable comprises an antenna, and the antenna is configured to facilitate a low power radiofrequency communication link between at least one of the implantable modules and an external programming module.

29. A method of implanting a tissue stimulation system comprising:
implanting a transmitter module, wherein the transmitter module comprises a transducer array comprising one or more ultrasound transducers;
implanting a separate battery module, wherein the battery module comprises a battery;
connecting the transmitter module and the battery module using an implantable cable;
wherein the battery module supplies power to the transmitter module; and
the transmitter module is configured to transmit acoustic energy towards one or more implantable receiver-stimulators that are in contact with the tissue for stimulating the tissue;
wherein the cable comprises an antenna, and the antenna is configured to facilitate a low power radiofrequency communication link between at least one of the implantable modules and an external programming module.

30. A method of implanting a tissue stimulation system comprising:
   implanting a separate battery module, wherein the battery module comprises a battery;
   connecting the battery module to an existing implanted transmitter module using an implantable cable;
   wherein the battery module supplies power to the transmitter module; and
   the transmitter module is configured to transmit acoustic energy towards one or more implantable receiver-stimulators that are in contact with the tissue for stimulating the tissue;
   wherein the cable comprises an antenna, and the antenna is configured to facilitate a low power radiofrequency communication link between at least one of the implantable modules and an external programming module.

31. The system as in claim 1, 8, or 28, wherein the transmitter module is a controller-transmitter; and
   wherein the antenna is configured to facilitate the communication link between the controller-transmitter and the external programming module.

32. The method as in claim 29, or 30, wherein the transmitter module is a controller-transmitter; and
   wherein the antenna is configured to facilitate the communication link between the controller-transmitter and the external programming module.

* * * * *